United States Patent [19]

Brazdil, Jr. et al.

[11] Patent Number: 4,515,732

[45] Date of Patent: May 7, 1985

[54] CONVERSION OF ACETONITRILE TO GLYCOLONITRILE AND/OR GLYCOLAMIDE

[75] Inventors: James F. Brazdil, Jr., Mayfield Village; William A. Marritt, Cleveland Heights; Michael D. Ward, South Euclid, all of Ohio

[73] Assignee: The Standard Oil Company, Cleveland, Ohio

[21] Appl. No.: 614,609

[22] Filed: May 29, 1984

[51] Int. Cl.$^3$ ............... C07C 121/36; C07C 103/167
[52] U.S. Cl. ................ 260/465.6; 260/465.8 R; 564/130
[58] Field of Search ................ 260/465.6; 564/130

[56] References Cited

U.S. PATENT DOCUMENTS 3,516,789  6/1970  Sennewald et al. ......... 260/465.3 X

OTHER PUBLICATIONS

Deutsch, et al.; J. Prakt. Chemie, 321(1), (1979), pp. 137–140.

Primary Examiner—Joseph Paul Brust
Attorney, Agent, or Firm—Charles S. Lynch; John E. Miller, Jr.; Larry W. Evans

[57] ABSTRACT

The vapor phase oxidation of acetonitrile with molecular oxygen in the presence or absence of water vapor to produce glycolonitrile or glycolamide.

3 Claims, No Drawings

CONVERSION OF ACETONITRILE TO GLYCOLONITRILE AND/OR GLYCOLAMIDE

This invention relates to a novel method of making glycolonitrile and/or glycolamide.

Heretofore glycolonitrile has been prepared by the reaction of formaldehyde with either hydrocyanic acid or with a mixture of water and sodium cyanide. Glycolonitrile can be hydrolyzed to glycolamide. Because of the relatively dangerous nature of inorganic cyanides, it is desirable to provide a process which does not require these starting materials. Moreover, acetonitrile is a product which is available in fairly large quantities as a by-product from other processes and it is of rather low value, and is thus an inexpensive starting material.

It is an object of the present invention to provide a new method for making glycolonitrile and/or glycolamide that does not utilize inorganic cyanides.

It is a further object of the present invention to provide a process for making glycolonitrile and/or glycolamide from acetonitrile.

Other objects, as well as aspects and advantages, of the invention will become apparent from a study of the specification and claims.

The foregoing objectives are realized by the present invention according to which there is provided a process which comprises the vapor phase oxidation of acetonitrile with molecular oxygen to produce glycolonitrile or glycolamide. When effected in the presence of water either or both glycolamide and glycolonitrile can be formed in a single step. The present inventors believe this reaction to be an entirely new reaction unknown before their discovery thereof.

The overall reaction going from acetonitrile to glycolonitrile or glycolamide (or both) requires one half mole of molecular oxygen gas. However, according to the invention it is contemplated that a deficiency of oxygen can be employed, as little as, for instance, one tenth mole per mole of acetonitrile, with unreacted acetonitrile being available for recycle. Usually no more than two moles of molecular oxygen are employed for each mole of acetonitrile, although higher ratios can be employed.

The reaction is effected at temperatures between 200° and 700° C., usually between 250° and 550° C. The gaseous molecular oxygen can of course be diluted with a nonreactive gas such as nitrogen; in this connection, air can of course be used. The reaction is effected by contacting the reactants with a solid heterogeneous oxidation catalyst, and can be carried out in a fixed bed, fluid bed, transfer line or a gravitating moving bed reactor. Reactor pressures are not critical and can be well below or well above atmospheric, but absolute pressures of 10 to 20 psi are usually employed.

It is a feature of the invention that one or both of fumaronitrile or maleonitrile are sometimes co-produced with the glycolonitrile and these useful products can be recovered and sold as such or converted to the corresponding diacids.

The following specific examples are illustrative only and demonstrate (1) the preparation of specific catalysts useful in the claimed process as well as (2) representative examples of the oxidation process of the present invention.

EXAMPLE 1

25.0 g. of $Sb_2O_3$ were oxidized in about 100 cc. of concentrated nitric acid by heating with constant stirring for 15 minutes, at which time 129.3 g. of $UO_2(NO_3)_2.6H_2O$ dissolved in about 150 cc. of water were added and heating and stirring were continued for another hour. During this hour 100 cc. more of water were added to the mixture. It was then cooled and neutralized with 218 cc. of concentrated aqueous ammonium hydroxide to pH of 8.0. A yellow precipitate was formed and the slurry was vacuum filtered, washed with water that contained a small amount of $NH_4OH$ and was dried overnight at about 130° C. The dried filter cake was thereafter heated at about 940° C. for 18 hours.

Before use as a catalyst in the oxidation of acetonitrile this catalyst was pretreated in a tubular fixed bed reactor containing 2 cc. of the catalyst by passing a gaseous mixture of steam, $O_2$ and $N_2$ thereover at respective flow rates of 0.5 g/min., 7.8 cc./min. and 122.4 cc./min. for 55 minutes while the catalyst bed was maintained at 400° C.

EXAMPLE 2

$NH_4VO_3$ (116.99 g.) was stirred in about 300 ml. of distilled water with low heat. Silical sol (69.27 g, 40% $SiO_2$) was added. Cupric nitrate $(Cu(NO_3)_2.2.5H_2O$, 58.15 g.) was then added. The resulting slurry was heated and stirred to remove part of the water. It was then heated at 120° C. overnight to dry the solids. The dried material was then denitrified by heating at 290° C. for 3 hours, followed by 425° C. for 3 hours. It was ground to 20–35 mesh particle size. The catalyst was 80% $Cu_{0.5}V_2O_x$ on 20 percent $SiO_2$ support.

EXAMPLE 3

$NH_4VO_3$ (116.99 g.) was dissolved in about 600 ml. of distilled water. Silica sol (56.84 g, 40% $SiO_2$) was added. The resulting slurry was then heated and stirred to remove part of the water. It was dried by heating overnight at about 120° C. The catalyst was then denitrified and ground as in Example 2. This catalyst was 80% $V_2O_5$ on 20% $SiO_2$ support.

EXAMPLE 4

$NH_4VO_3$ (116.99 g.) was stirred in about 300 ml of distilled water with low heat. Silical sol (69.27 g, 40% $SiO_2$) was added. Ferric nitrate $(Fe(NO_3)_3.9H_2O$, 20.2 g.). was then added. The resulting slurry heated and stirred to remove part of the water. It was then heated at 120° C. overnight to dry the solids. The dried material was then denitrified by heating at 290° C. for 3 hours, followed by 425° C. for 3 hours. It was ground to 20–35 mesh particlesize. This catalyst was 80% $Fe_{0.1}V_2O_x$ on 20 percent $SiO_2$ support.

EXAMPLE 5

Magnesium nitrate (256.86 g.) was dissolved in a 150 ml distilled $H_2O$. Silica sol (25.19 g, 40% $SiO_2$) was added. Concentrated ammonium hydroxide (200 ml) was added slowly with stirring. The resulting slurry was filtered and washed 6 times with $H_2O$ containing a small amount of ammonium hydroxide. It was filtered and allowed to suction overnight.

The catalyst was ground to between 20–35 mesh particle size. It was placed in a tube furnace equipped with a dry ice/acetone bath and vacuum. While a vacuum was pulled, the catalyst was slowly heated (raised 40° C./½ hour) to 450° C. it was allowed to cool under vacuum and then stored in a dessicator. It was 80% MgO on 20% silica support.

wool plugs. The tube was situated vertically between two halves of a thermostatically controlled heating block. The reaction conditions and results are given in Table 1.

TABLE 1

| Example No. | Catalyst of Example | Temperature, °C. | Contact Time, Secs. | Mol Ratios $CH_3CN/O_2/N_2/H_2O$ | Acetonitrile Conversion, Percent | Yields, Percent | | Selectivities | |
|---|---|---|---|---|---|---|---|---|---|
| | | | | | | Glycolonitrile | Glycolamide | Glycolonitrile | Glycolamide |
| 8 | 1 | 400 | 0.5 | 1/0.25/4.74/0 | 2.9 | 0.7 | 0 | 24.1 | 0 |
| 9 | 2 | 350 | 0.11 | 1/0.6/10.5/1.3 | 16.1 | 4.65 | 0 | 29.0 | 0 |
| 10 | 3 | 300 | 1.3 | 1/0.6/11.4/1.3 | 26.4 | 6.8 | 0 | 25.6 | 0 |
| 11 | 4 | 350 | 0.11 | 1/0.6/10.5/1.3 | 11.1 | 3.64 | 5.55 | 3.64 | 50.2 |
| 12 | 5 | 300 | 9.28 | 1/0.4/7.8/1.3 | 4.6 | 0.4 | 1.55 | 8.65 | 33.5 |
| 13 | 6 | 350 | 1.06 | 1/0.5/9.5/1.3 | 35 | 1.7 | 0 | 4.9 | 0 |
| 14 | 7 | 300 | 0.14 | 1/0.7/13.2/1.3 | 9.9 | 0 | 4.52 | 0 | 45.7 |
| 15 | 3 | 375 | 0.15 | 1/0.6/11.4/1.3 | 8.7 | 0 | 4.9 | 0 | 56 |
| 16 | 4 | 375 | 0.11 | 1/0.53/10.83/0 | 28.3 | 1.82 | 0 | 6.42 | 0 |

EXAMPLE 6

Cupric nitrate ($Cu(NO_3)_2.2.5H_2O$, 233.6 g) was dissolved in 200 ml distilled $H_2O$. $SiO_2$ sol (49.71 g, 40% $SiO_2$) was then added to this solution. It was heated and stirred to remove part of the water. It was then dried overnight at 120° C. The product was 80% CuO on 20% silica support.

The catalyst was denitrified and ground as in Example 4.

EXAMPLE 7

Ammonium vanadate ($NH_4VO_3$, 2.34 g) was dissolved in about 50 ml. water. Particulate alumina (16.37 g.) was impregnated by about ¼ of the $NH_4VO_3$ solution for four times, drying being effected after each impregnation at 120° C. for periods of 4–16 hours. The final drying was overnight. The dried catalyst was denitrified as in Example 4. The catalyst was 10 percent $V_2O_5$ on 90% alumina support.

The following examples in Table 1 were effected in a tubular fixed bed reactor containing 2 cc. of the solid granular catalyst. The reactor was a ⅜ inch I.D. stainless steel tube, and the catalyst was held in place by glass In Table 1, the yields are the percent of acetonitrile converted to the indicated product, while selectivities are the percent of the converted or reacted acetonitrile which was converted to the indicated product.

As will be evident to those skilled in the art, various modifications of this invention can be made or followed in the light of the foregoing disclosure and discussion without departing from the spirit and scope of the disclosure or from the scope of the claims.

We claim:

1. The vapor oxidation of acetonitrile with molecular oxygen in the presence or absence of water vapor and in the presence of a solid heterogeneous oxidation catalyst to produce glycolonitrile or glycolamide, wherein (1) glycolamide is produced only when water is present and (2) said acetonitrile, oxygen and water are the sole reactants present.

2. The vapor phase oxidation of claim 1 wherein the temperature of the oxidation reaction is in the range from 200° to 700° C.

3. The vapor phase oxidation of claim 1 wherein the temperature of the oxidation reaction is in the range from 250° to 550° C.

* * * * *